(12) United States Patent
Chen et al.

(10) Patent No.: US 9,222,869 B2
(45) Date of Patent: Dec. 29, 2015

(54) SHEATH FLOW DEVICE AND HEMATOLOGY ANALYZER

(71) Applicant: SonoScape Co., Shenzhen, Guangdong (CN)

(72) Inventors: Yunliang Chen, Guangdong (CN); Zhengguo Jiang, Guangdong (CN); Guohu Liu, Guangdong (CN)

(73) Assignee: SONOSCAPE CO., Shenzhen, Guangdong (CN)

( * ) Notice: Subject to any disclaimer, the term of this patent is extended or adjusted under 35 U.S.C. 154(b) by 0 days.

(21) Appl. No.: 14/414,689

(22) PCT Filed: Apr. 3, 2013

(86) PCT No.: PCT/CN2013/073686
§ 371 (c)(1),
(2) Date: Jan. 13, 2015

(87) PCT Pub. No.: WO2014/023105
PCT Pub. Date: Feb. 13, 2014

(65) Prior Publication Data
US 2015/0177117 A1  Jun. 25, 2015

(30) Foreign Application Priority Data

Aug. 9, 2012 (CN) .......................... 2012 1 0282286

(51) Int. Cl.
*G01N 33/48* (2006.01)
*G01N 15/12* (2006.01)
*G01N 15/14* (2006.01)
*G01N 33/49* (2006.01)

(52) U.S. Cl.
CPC ........ *G01N 15/1218* (2013.01); *G01N 15/1436* (2013.01); *G01N 33/49* (2013.01); *G01N 33/4915* (2013.01)

(58) Field of Classification Search
CPC ... G01N 33/49; G01N 15/05; G01N 15/1434; A61B 5/14532; A61B 5/1455
USPC ............................................................. 356/39
See application file for complete search history.

(56) References Cited

U.S. PATENT DOCUMENTS 6,819,411 B1 * 11/2004 Sharpe et al. ................... 356/72
2008/0106736 A1 * 5/2008 Graves et al. ................. 356/338

FOREIGN PATENT DOCUMENTS

| CN | 102308196 A | 1/2012 |
|---|---|---|
| CN | 203572751 U | 4/2014 |
| EP | 2264428 A2 | 12/2010 |
| JP | 7-504497 | 5/1995 |
| JP | 2010-276363 | 12/2010 |

* cited by examiner

*Primary Examiner* — Tarifur Chowdhury
*Assistant Examiner* — M D Rahman
(74) *Attorney, Agent, or Firm* — Han IP Corporation

(57) ABSTRACT

An embodiment of a sheath flow device may include: a reflecting plane, aspheric reflecting surface, and a conduit for passage of cells disposed in a central hollow. A focal point of the aspheric reflecting surface is positioned in a location where cells settle. A collimated beam generated by an external light source incident on a first reflective side of the reflecting plane, is reflected to reach a first reflective surface of the aspheric reflecting surface, and reflected before being focused on the focal point, after which the light proceeds to reach a second reflective surface of the aspheric reflecting surface to be reflected to reach a second reflective side of the reflecting plane to emerge after being reflected thereby. The first and second reflective sides and the first and second reflective surfaces may be centrosymmetric. The sheath flow device improves the alignment accuracy of beam commissioning during the application process.

13 Claims, 7 Drawing Sheets ized by an external light source incident on a first reflective side of the reflecting plane is reflected thereby to reach a first reflective surface of the aspheric reflecting surface, and is reflected thereby before being focused on the focal point to reach a second reflective surface of the aspheric reflecting surface to be reflected thereby to reach a second reflective side of the reflecting plane to emerge after being reflected thereby. The first and second reflective sides of the reflecting plane and the first and second reflective surfaces of the aspheric reflecting surface may be centrosymmetric.

SHEATH FLOW DEVICE AND HEMATOLOGY ANALYZER

CROSS REFERENCE TO RELATED PATENT APPLICATIONS

The present application is the U.S. national stage application of PCT Patent Application No. PCT/CN2013/073686, filed on Apr. 3, 2013, which was filed based on and claims the priority benefit of China Patent Application No. 201210282286.8, filed on Aug. 9, 2012. The above applications are herein incorporated by reference in their entirety.

TECHNICAL FIELD

The present disclosure relates to the technical field of medical devices and, more specifically, to a sheath flow device and hematology analyzer.

BACKGROUND

The vast majority of contemporary flow hematology analyzers measure the scattered or transmitted signals from cells exposed to optical radiation so as to acquire information on the volume and an internal structure of the cells. Their specific work process can be summarized as follows: An emitting optical system is employed to focus a beam emitted from a light source into a hollow sheath flow chamber, wherein fluid focusing principles are exploited to force cells in sequence through a focal region. Light transmitted or scattered by the cells is collected by a receiving optical system on a photoelectric detector, where the optical signals are further subjected to data processing so as to obtain the desired information on cell volume, internal structure and the like. The structure of a typical hematology analyzer optical system device is shown in FIG. 1. In such a system, the emitting optical system and receiving optical system are typically composed of one or more optical lenses.

When using a hematology analyzer optical system device of the type shown in FIG. 1, during the actual commissioning and production process it is necessary to accurately align the center of the light spots obtained by focusing the emitting optical system with the position of the cells in the sheath flow chamber, i.e., the x, y and z coordinates of the optical system all need to be aligned.

In traditional optical systems, as the optical paths arising from mutual coupling of multiple degrees of freedom make alignment difficult, in actual production it is necessary to employ a dedicated alignment apparatus and commissioning procedure, which lowers production efficiency and increases the cost of production. Not only this, but the emitting and receiving optical systems are also required to possess light source shaping and focusing functions, so that multiple (e.g., four to six) optical transmission lenses are necessary to achieve the desired image quality. Multi-lens optical systems also require precise tuning, and are further hampered by constraints such as complex commissioning and long processing times.

SUMMARY

In view thereof, the embodiments of the present disclosure provide a sheath flow device and hematology analyzer which can improve alignment accuracy of beam commissioning during application.

In one aspect, a sheath flow device may include a reflecting plane, an aspheric reflecting surface comprising a focal point, and a conduit comprising a central hollow and configured to allow passage of cells disposed in the central hollow. The focal point of the aspheric reflecting surface may be positioned in a location where the cells settle. The reflecting plane and the aspheric reflecting surface may be configured such that a collimated beam generated by an external light source incident on a first reflective side of the reflecting plane is reflected thereby to reach a first reflective surface of the aspheric reflecting surface, and is reflected thereby before being focused on the focal point to reach a second reflective surface of the aspheric reflecting surface to be reflected thereby to reach a second reflective side of the reflecting plane to emerge after being reflected thereby. The first and second reflective sides of the reflecting plane and the first and second reflective surfaces of the aspheric reflecting surface may be centrosymmetric.

In some embodiments, the sheath flow device may further include a transmission plane adjoining the reflecting plane. The transmission plane may be configured such that a parallel light vertically incident on a first transmissive side of the transmission plane is transmitted thereby to reach the first reflective side of the reflecting plane, reflected thereby to reach the first reflective surface of the aspheric reflecting surface, and reflected thereby before being focused on the focal point to reach the second reflective surface of the aspheric reflecting surface to be reflected thereby to reach the second reflective side of the reflecting plane, and to be reflected thereby to reach a second transmissive side of the transmission plane to be transmitted. The first and second transmissive sides of the transmission plane, the first and second reflective sides of the reflecting plane, and the first and second reflective surfaces of the aspheric reflecting surface may be centrosymmetric.

In some embodiments, the aspheric reflecting surface may be a rotating parabolic surface.

In some embodiments, an angle between the first transmissive side and the first reflective side may be 45 degrees, and an angle between the second transmissive side and the second reflective side may be 45 degrees.

In some embodiments, the reflecting plane may be a total reflecting plane.

In some embodiments, the aspheric reflecting surface may be coated with an optical reflective film.

In some embodiments, the transmission plane, the reflecting plane, the aspheric reflecting surface, and the conduit may be made of a same optical material.

In some embodiments, the transmission plane may be coated with an anti-reflection film.

In some embodiments, the reflecting plane, the aspheric reflecting surface, and the conduit may be an integrally formed structure.

In some embodiments, the reflecting plane, the aspheric reflecting surface, the transmission plane, and the conduit may be an integrally formed structure.

In another aspect, a hematology analyzer may include a light source, an emitting optical system, a receiving optical system, a detector, and a sheath flow device. The sheath flow device may include a reflecting plane, an aspheric reflecting surface comprising a focal point, and a conduit comprising a central hollow and configured to allow passage of blood cells disposed in the central hollow. The focal point of the aspheric reflecting surface may be positioned in a location where the blood cells settle. The reflecting plane and the aspheric reflecting surface may be configured such that a collimated beam generated by an external light source incident on a first reflective side of the reflecting plane is reflected thereby to reach a first reflective surface of the aspheric reflecting surface, and is reflected thereby before being focused on the focal point to reach a second reflective surface of the aspheric reflecting surface to be reflected thereby to reach a second reflective side of the reflecting plane to emerge after being reflected thereby. The first and second reflective sides of the reflecting plane and the first and second reflective surfaces of the aspheric reflecting surface may be centrosymmetric. A parallel light generated by the light source may be collimated by the emitting optical system before entering the sheath flow device to be focused on a position where blood cells are located therein. A light transmitted or scattered by the blood cells may be received by the receiving optical system and output to the detector, which carries out blood analysis based on the transmitted or scattered light.

In some embodiments, the light source may include a laser, a halogen lamp or a light-emitting diode.

In some embodiments, the emitting optical system may include a single collimating lens.

In some embodiments, the receiving optical system may include a single collimating lens.

In the embodiments of the present disclosure, the integration of a reflecting plane and aspheric reflecting surface in the sheath flow device allow collimated beam incident on the sheath flow chamber to be automatically reflected by the reflecting plane, reflecting the beam onto the aspheric reflecting surface to be reflected thereby and then focused onto the location of the cells. It may be appreciated that in the operation of this device, it is only necessary to adjust the degrees of freedom for the incident light beam, enabling considerable increases in the alignment accuracy of beam commissioning during application, while also reducing the complexity of the emitting and receiving optical systems which accompany the present device, lowering the difficult of production and commissioning.

The embodiments and advantages will be more readily appreciated as the same becomes better understood by reference to the following detailed description and the accompanying drawings showing exemplary embodiments, in which like reference symbols designate like parts. For clarity, various parts of the embodiments in the drawings are not drawn to scale.

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily in scale as some components may be shown to be out of proportion than the size in actual implementation in order to clearly illustrate the concept of the present disclosure.

DETAILED DESCRIPTION OF PREFERRED EMBODIMENTS

Figure 1:
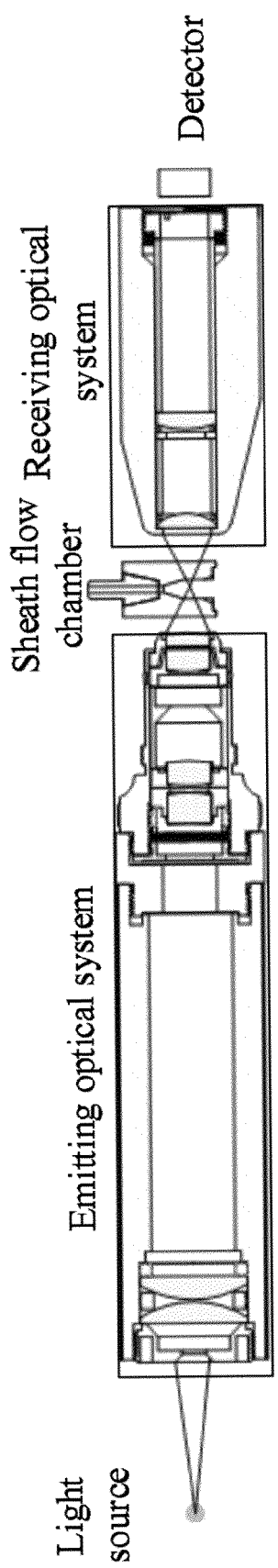
FIG. 1 is a structural schematic of a hematology analyzer optical system device typical in the prior art.

What follows is a clear and complete description of the technical solutions in the embodiments of the present disclosure with reference to the drawings therein. It will be readily appreciated that the embodiments described herein are merely some and not all of the embodiments of the present disclosure. Any other embodiments which those persons of ordinary skill in the art could arrive at from the embodiments of the present disclosure without expending creative labor shall fall within the protective scope of the present disclosure.

First, a sheath flow device provided by the present disclosure will be described. Such a device may be constructed with components including, for example: a reflecting plane, an aspheric reflecting surface, and a conduit for the passage of cells disposed in a central hollow. A focal point of the aspheric reflecting surface is positioned in a location where the cells settle. Collimated beam generated by an external light source is incident on a first reflective side of the reflecting plane, and is reflected thereby to reach a first reflective surface of the aspheric reflecting surface. The collimated beam is reflected thereby before being focused on the focal point position, after which the beam proceeds to reach a second reflective surface of the aspheric reflecting surface to be reflected thereby to reach a second reflective side of the reflecting plane and to emerge after being reflected thereby. The first and second reflective sides and the first and second reflective surfaces may all be centrosymmetric.

In some embodiments of the present disclosure, the integration of a reflecting plane and an aspheric reflecting surface in the sheath flow device allow collimated beam incident on the sheath flow chamber to be automatically reflected by the reflecting plane. In particular, the collimated beam is reflected onto the aspheric reflecting surface to be reflected thereby and then focused onto the location of the cells. It may be appreciated that in the operation of this device, it is only necessary to adjust the degrees of freedom for the incident light beam, enabling considerable increases in the alignment accuracy of beam commissioning during application. This also reduces the complexity of the emitting and receiving optical systems which accompany the present device, thus lowering the difficult of production and commissioning.

In actual application, the foregoing sheath device may further comprise a transmission plane adjoining the reflecting plane, such that collimated beam is vertically incident on a first transmissive side of the transmission plane to be transmitted thereby to reach the first reflective side of the reflecting plane. The collimated beam is reflected thereby to reach the first reflective surface of the aspheric reflecting surface to be reflected thereby before being focused on the focal point position. After which the light proceeds to reach the second reflective surface of the aspheric reflecting surface to be reflected thereby to reach the second reflective side of the reflecting plane, where the collimated beam is reflected thereby to reach a second transmissive side of the transmission plane to be transmitted. The first and second transmissive sides, the first and second reflective sides, and the first and second reflective surfaces may all be centrosymmetric.

Specifically, once incorporating a transmission plane, it is possible to coat the transmission plane with an anti-reflection film. Moreover, the aspheric reflecting surface may be a rotating parabolic surface. The angle between the first transmissive side and the first reflective side, as well as the angle between the second transmissive side and the second reflective side, may be 45 degrees.

In order to increase the intensity of reflected light, the reflecting plane in the foregoing sheath flow device may be a total reflecting plane. Further, the aspheric reflecting surface may be coated with an optical reflective film, which further enhances the intensity of light focused on the cells.

Preferably, the aforementioned sheath flow device may be an integrally formed structure, e.g., a monolithic structure entirely made from the same optical material such as, for example, optical plastic or optical glass, etc. The device may be manufactured by such means as cold or hot processing.

As optical plastic can be mass produced by techniques such as injection molding or compression molding, and is inexpensive and can ensure favorable mechanical precision. Thus, this is the preferred material for the foregoing sheath flow device.

To facilitate understanding of the sheath flow device, specific examples are utilized herein to provide a detailed description of the overall solution.

Figure 2A:
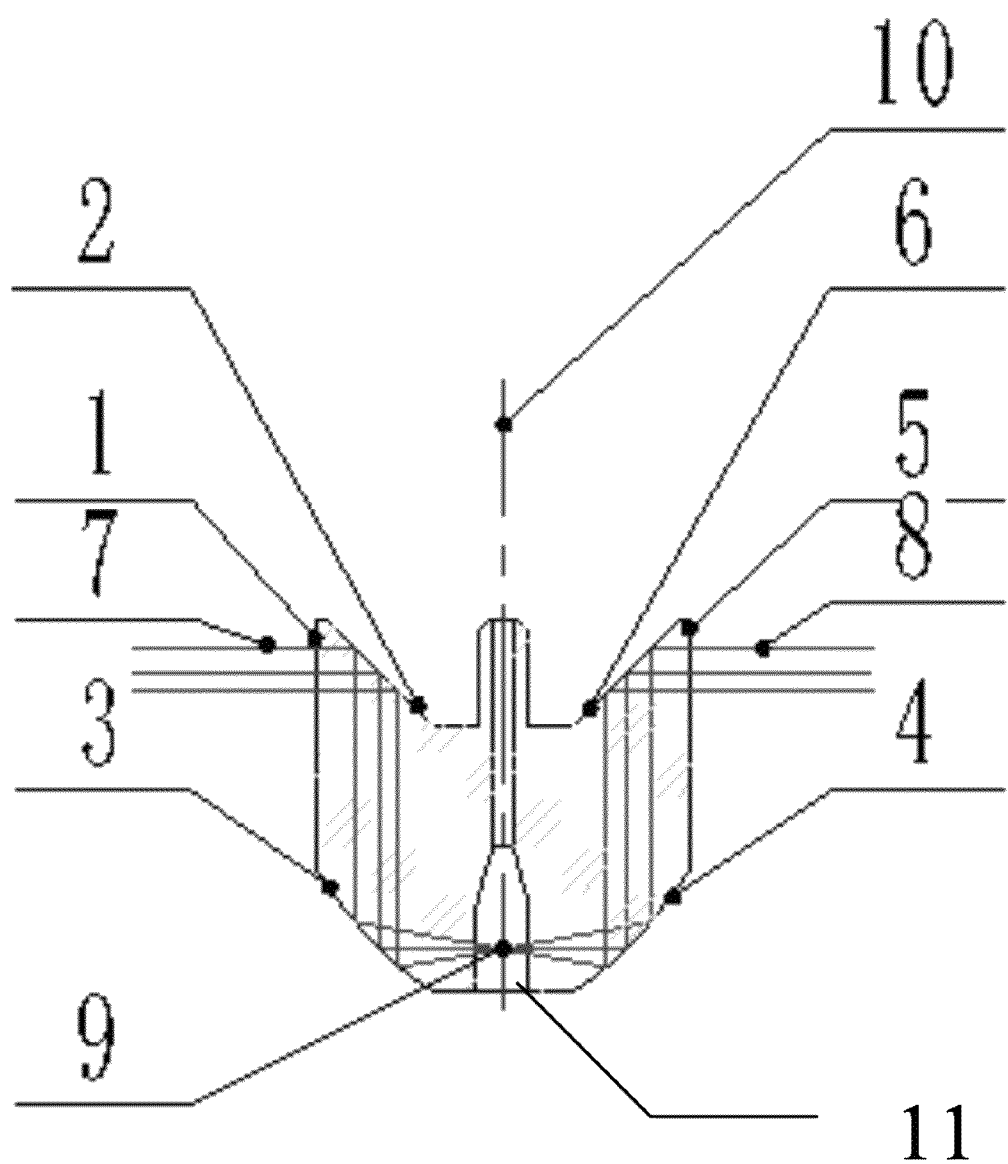
FIG. 2A is a side view of a sheath flow device provided by an embodiment of the present disclosure.
Figure 2B:
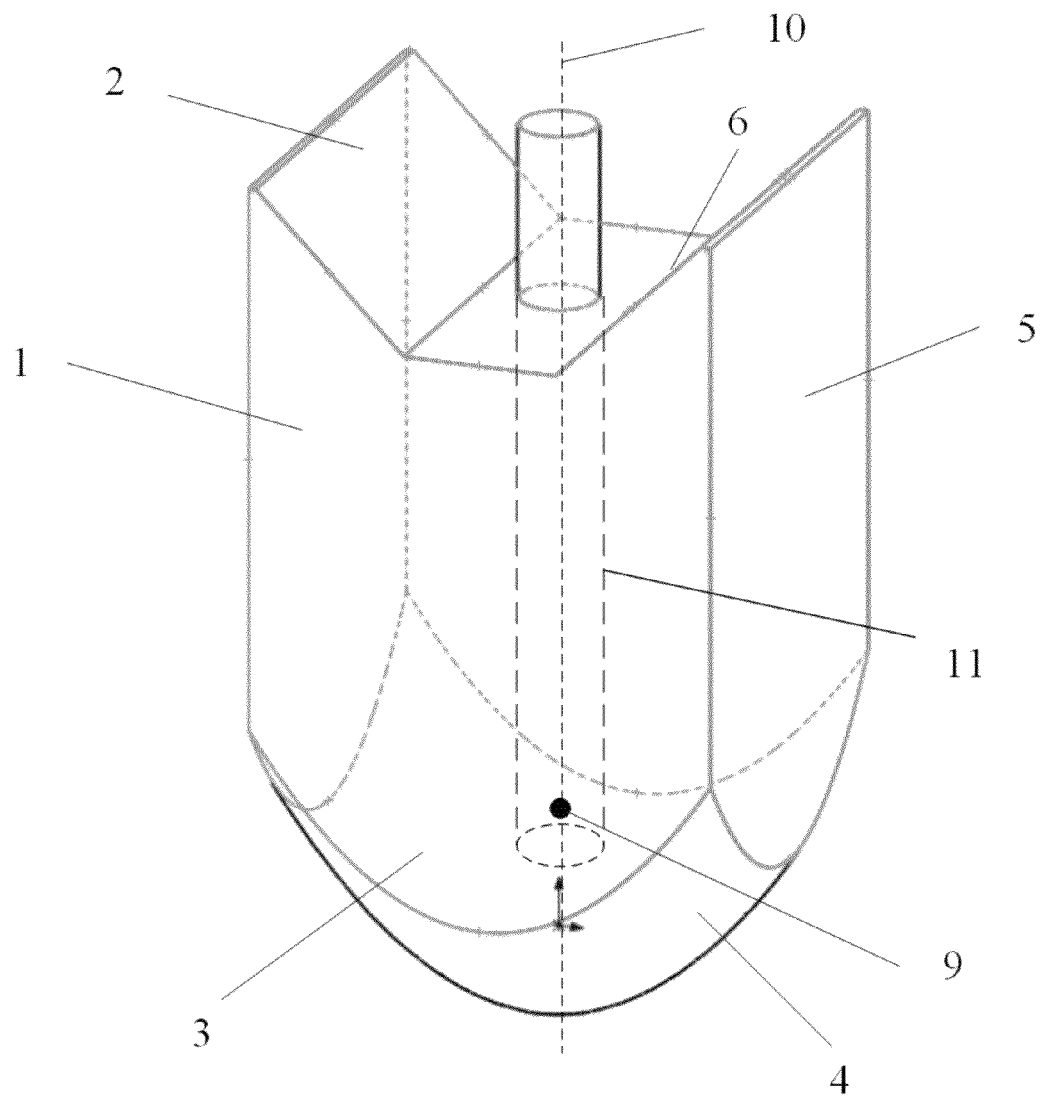
FIG. 2B is a three dimensional view of the sheath flow device in FIG. 2A.

As shown by the side view of the sheath flow device given in FIG. 2A, the sheath flow device is a solid object that includes an optical transmission plane, a reflecting plane and an aspheric reflecting surface. The center of gravity of the solid object is provided with a hollow conduit 11, the conduit 11 being the passage for the flow and focusing of cells. As shown in FIG. 2A, numeral reference 1 indicates the first transmissive side of the optical transmission plane, numeral reference 2 indicates the first reflective side of the optical reflecting plane, numeral reference 3 indicates the first reflective surface of the aspheric reflecting surface, numeral reference 4 indicates the second reflective surface of the aspheric reflecting surface, numeral reference 5 indicates the second transmissive side of the optical transmission plane, numeral reference 6 indicates the second reflective side of the optical reflecting plane, numeral reference 7 indicates the incident beam, numeral reference 8 indicates the emergent beam, numeral reference 9 indicates the focal point of the aspheric reflecting surface, and numeral reference 10 indicates the center axis. FIG. 2B is a three-dimensional view of the sheath flow device shown in FIG. 2A.

The first transmissive side 1 and second transmissive side 5, the first reflective side 2 and second reflective side 6, and the first reflective surface 3 and second reflective surface 4 may all be centrosymmetrical. That is, sides 1 and 5 may be parallel with central axis 10, sides 2 and 6 may be disposed at 45 degree angles to central axis 10, sides 1 and 2 may be disposed at a 45 degree angle to each other, and sides 5 and 6 may be disposed at a 45 degree angle to each other. Sides 2, 3, 4, and 6 are all optical reflecting faces. In some embodiments, sides 2 and 6 may be totally reflecting surface which exploit the total reflection effect, and sides 3 and 4 may be coated with optical reflective film. In some embodiments, sides 1 and 5 may be coated with anti-reflection film.

The operation of the foregoing sheath flow device is now described. Collimated beam 7 is vertically incident on first transmissive side 1 to be reflected first by first reflective plane 2, and then by first reflective surface 3. First reflective surface 3 focuses the light beam on focal point 9, which is the target point i.e., the location of the cells. At the focal point, the light beam interacts with the cells and is projected onto second reflective surface 4, which collimates the beam and projects it onto second reflective plane 6. Second reflective plane 6 reflects the beam, and the reflected beam passes through second transmissive side 5 to become emergent beam 8.

Figure 3:
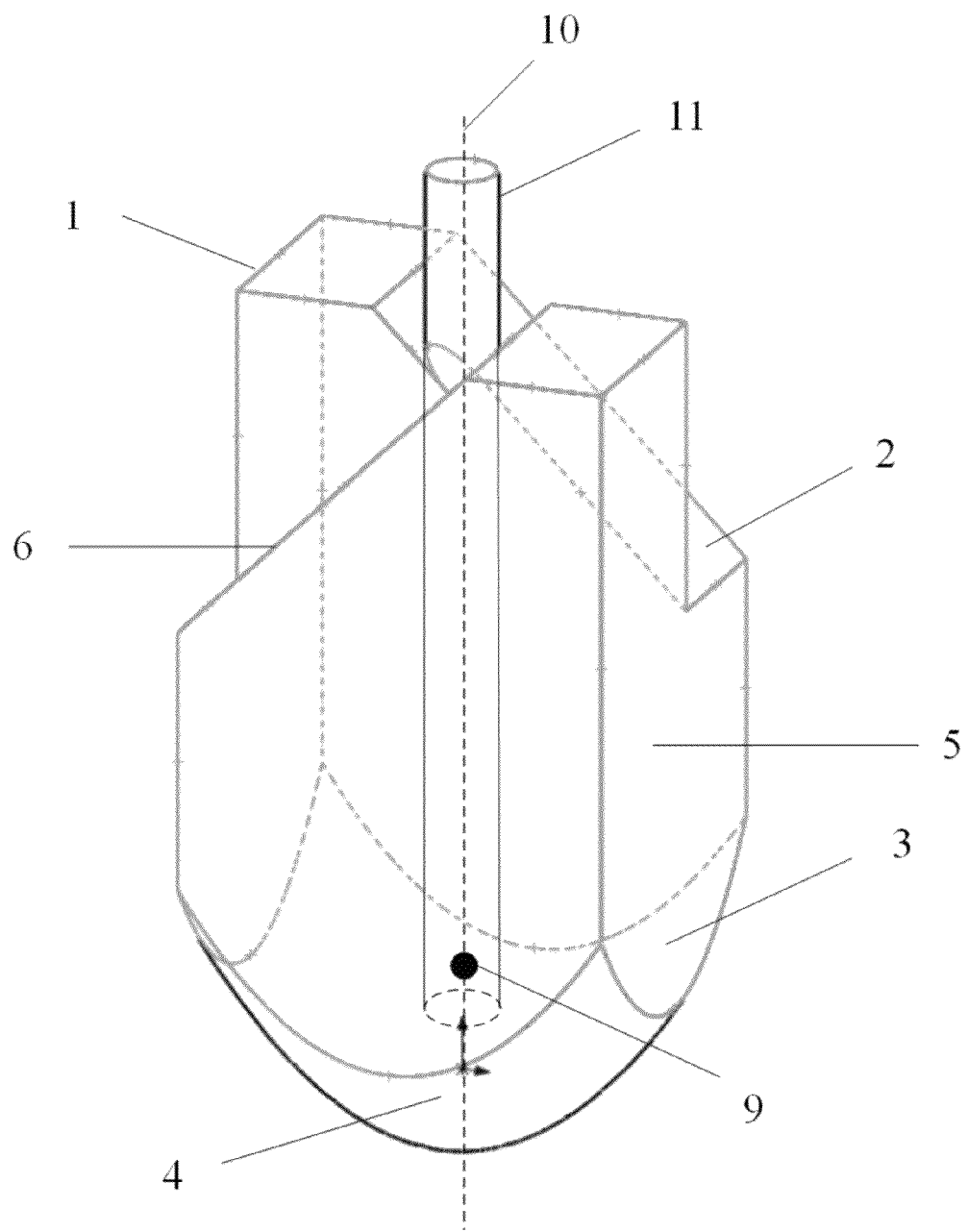
FIG. 3 is a schematic diagram of another sheath flow device provided by an embodiment of the present disclosure.

Of course, in actual application, the positioning of first transmissive side 1 and first reflective plane 2, as well as that of second transmissive side 5 and second reflective plane 2, is by no means limited to the layout depicted in FIGS. 2A and 2B, as other designs are also possible, such as that depicted in FIG. 3. Any arrangement that satisfies the requirements of a 45-degree angle between sides 1 and 2 and between sides 5 and 6 will suffice.

The working principle of the sheath flow device of the present disclosure is described in further detail below with reference to FIG. 4. As both the first transmissive side 1 and first reflective plane 2 are optical planes that do not alter the properties of a light beam, their inclusion is made in consideration of structural rationality. As the various optical faces are arranged symmetrically around central axis 10, in the interest of brevity only light incidence of the left side is described herein, and it may be appreciated that the same principles apply to emergence on the right side.

Figure 4:
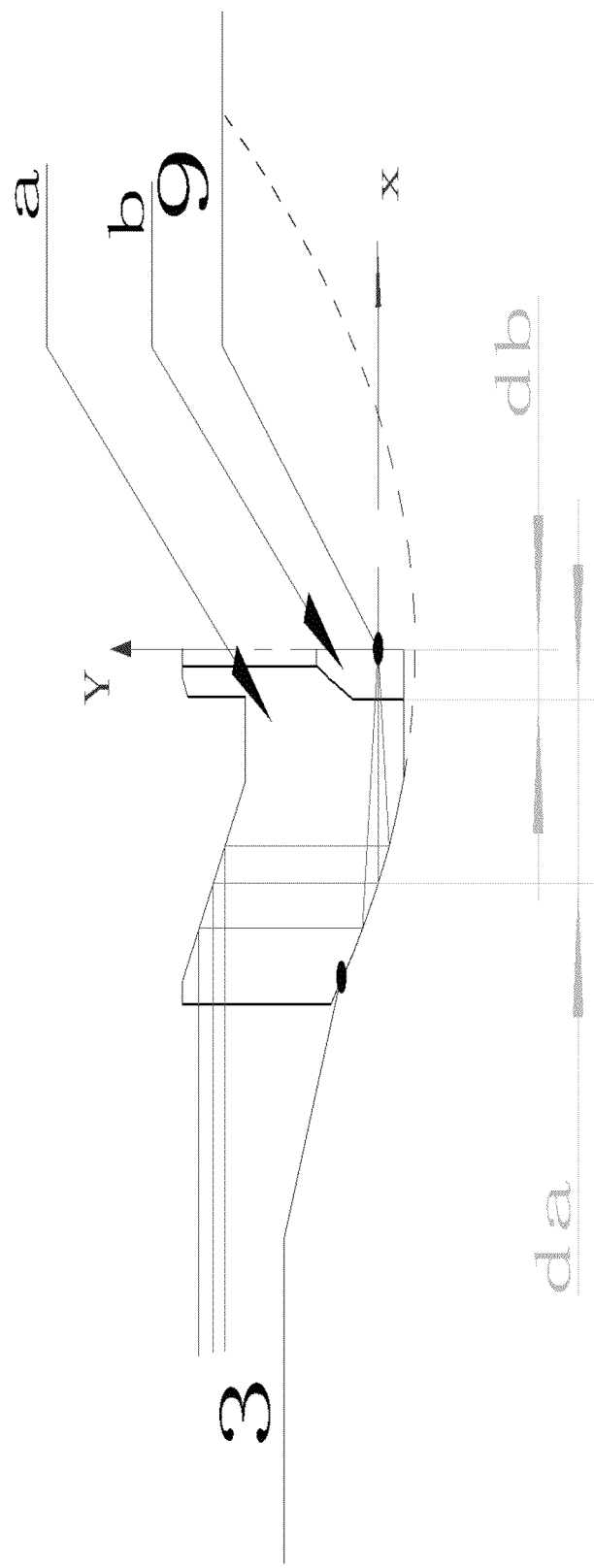
FIG. 4 is a working principle diagram of a sheath flow device provided by an embodiment of the present disclosure.

In FIG. 4, alphabetical reference "a" indicates the material from which the device is made, which has a refractive index of $n_a$, alphabetical reference "b" indicates the space for the fluid sample to be tested, with a refractive index of $n_b$, while alphabetical references "da" and "db" indicate the distances illustrated in the diagram. The first reflective surface 3 may be a parabolic surface or part thereof formed by a parabolic line revolving around axis 10. In the coordinate system established in FIG. 4, the origin of the coordinates is focal point 9. The parabolic curve in optical surface 3 may be described by Equation (1) below:

$$y = -\frac{p}{2} + \frac{1}{2p}(x-q)^2 \qquad (1)$$

Setting the incident beam waist as $\omega_0$, the spot beam waist expected at focal point 9 is $\omega_1$, and the wavelength of the beam in a vacuum is $\lambda_0$. Once $n_a$ $n_b$ $d_b$ are known, the parameters in Equation Error! Reference source not found. may be found from Equations (2) and (3) below.

$$p = \frac{\pi \omega_0 \omega_1 n_a}{\lambda_0} \qquad (2)$$

$$d_a = p - d_b \cdot \frac{n_a}{n_b} \qquad (3)$$

Equation Error! Reference source not found. ensures that spot shapes of desirable sizes may be obtained, while Equations (2) and (3) ensure that the focal point of the parabolic surface coincides with the location of the cells. The sheath flow device in the embodiments of the present disclosure is ideal for focusing incident collimated beam onto the position of cells, i.e., the focal point of the aspheric reflecting surface.

Figure 5:
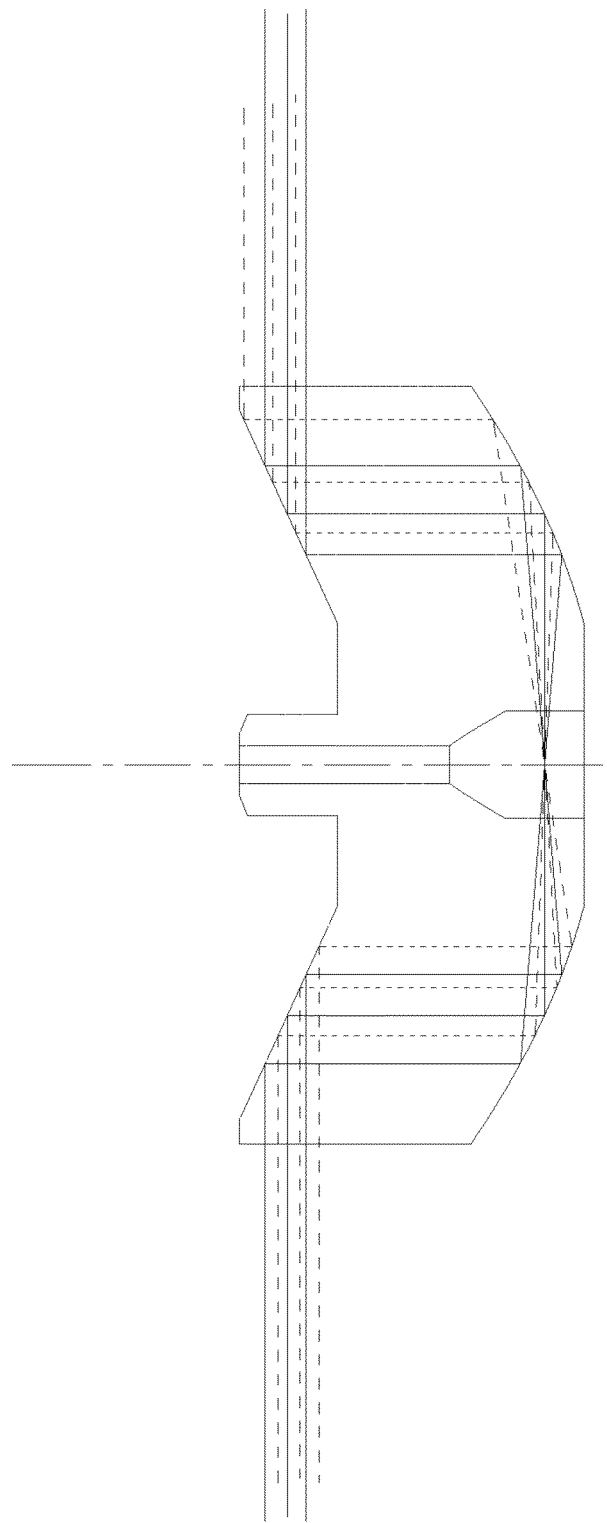
FIG. 5 is a diagram depicting deviation of light beams in the sheath flow device of an embodiment of the present disclosure.

Error! Reference source not found. illustrates a representation of the beam deviation, where the solid lines in the diagram represent the ideal beam, and the dotted lines indicate deviant beams. It may be appreciated from FIG. 5 that, due to the parabolic nature of the surface, the light beam remains focused on the focal point even after horizontal deviation.

Accordingly, when using the foregoing sheath flow device in actual commissioning, it is only necessary to ensure that the axes of the incident collimated beam are perpendicular to first transmissive side 1. This greatly reduces the difficulty of commissioning associated with traditional optical systems, where it is necessary to conduct alignment in at least two dimensions. Furthermore, as the present device is preferably made from optical plastic integrally formed, it is possible to favorably guarantee the positional accuracy of all the optical faces, and the device is not sensitive to environmental influences, making it well suited to ensuring the accuracy requirements imposed on instrumentation. In terms of cost, mass production of integrally formed optical plastic devices can greatly reduce component costs and ensure conformity of production. In addition, both the incident and emergent beams in the device are required to be parallel beams, where laser light can typically be collimated with a single lens optical system, which also considerably reduces the number of components over the four to six lens system required by traditional devices, thus further lowering costs.

Due to the differences between theory and optical systems in actual practice, the above Equations (1), (2) and (3) only provide initial values for design, and there is likely to be some discrepancy with an optical system which has undergone optimization in an application setting. Cases where the magnitude of this discrepancy does not exceed 20% shall be regarded as coming under the scope of the present disclosure.

A laser, halogen lamp or light emitting diode, etc. may be employed as the light source used with the foregoing sheath flow device. As lasers have high brightness and favorable beam properties, they are the preferred light source for the sheath flow device.

Figure 6:
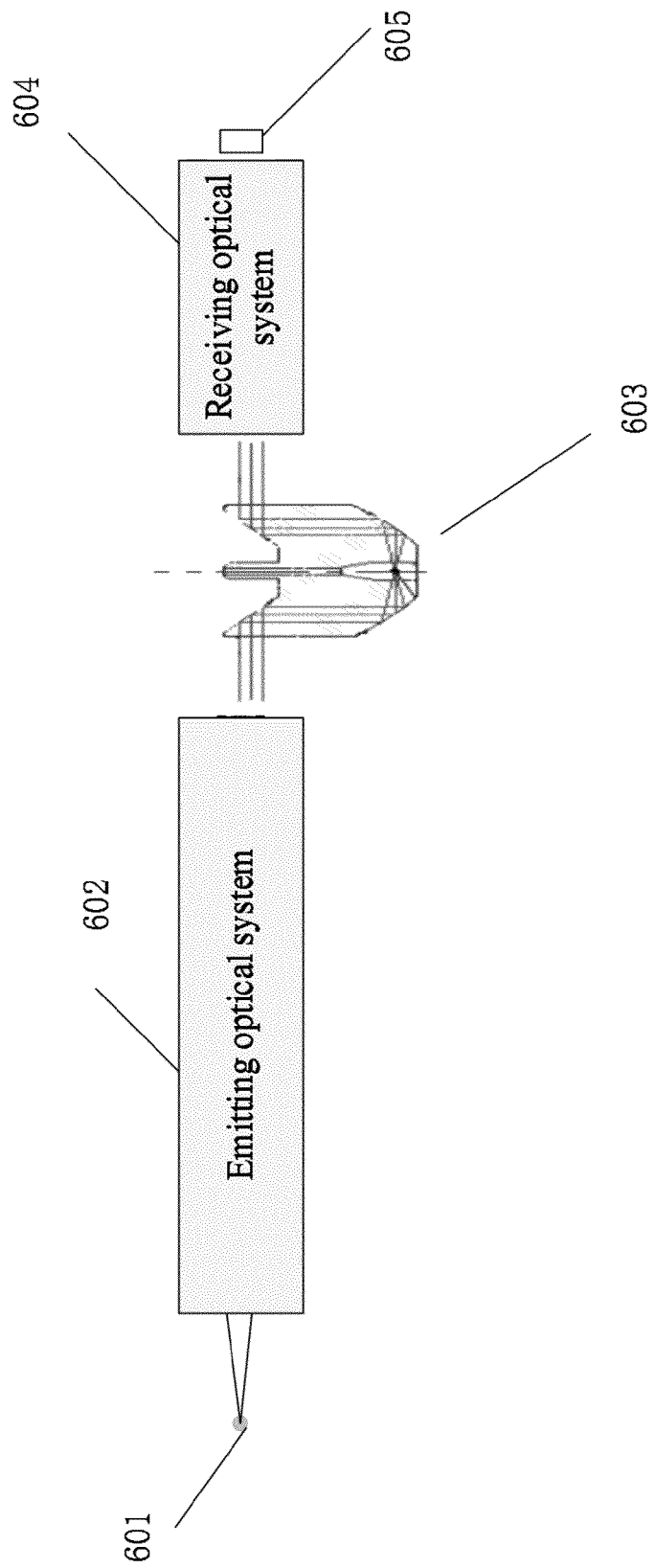
FIG. 6 is a structural diagram of a blood analyzer provided by an embodiment of the present disclosure.

The present disclosure further provides embodiments for a hematology analyzer corresponding to the sheath flow device. As shown in FIG. 6, an embodiments of a hematology analyzer may be constructed of components including the following: light source 601, emitting optical system 602, receiving optical system 604, detector 605 and the aforementioned sheath flow device 603. Collimated beam generated by the light source 601 is collimated by the emitting optical system 602 before entering the sheath flow device 603 to be focused on the position where blood cells are located therein. Light transmitted or scattered by the blood cells is received by the receiving optical system 604 and output to the detector 605, which carries out blood analysis based on the transmitted or scattered light.

In the hematology analyzer, the emitting optical system may comprise a single collimating lens. Further, the receiving optical system may also comprise just a single collimating lens.

As both the incident and emergent beams in the sheath flow device are required to be parallel beams, a single lens optical system may be directly utilized to collimate the incident and emergent light, such that the inclusion of a single collimating lens is sufficient for both the emitting optical system and the receiving optical system. This greatly reduces the number of components in comparison to the four to six lenses required by traditional optical systems.

A laser, halogen lamp or light emitting diode, etc. may be employed as the light source used with the foregoing sheath flow device. As lasers have high brightness and favorable beam properties, they are the preferred light source for the sheath flow device.

The specific implementation of the detector 605 in conducting blood analysis based on transmitted or scattered light is known to those persons in the art, and will not be elaborated herein in the interest of brevity.

The above description of the disclosed embodiments is made for the purposes of enabling persons skilled in the art to implement or use the present disclosure. Various modifications of these embodiments will be apparent to such persons skilled in the art, and the generic principles defined herein could be implemented in other embodiments without departing from the spirit or scope of the disclosed embodiments. Accordingly, the embodiments of the present disclosure shall not be limited to the embodiments cited herein, but shall be accorded the broadest scope consistent with the principles and novel features disclosed herein.

What is claimed is:

1. A sheath flow device, comprising:
    a reflecting plane;
    an aspheric reflecting surface comprising a focal point;
    a conduit comprising a central hollow and configured to allow passage of cells disposed in the central hollow; and
    a transmission plane adjoining the reflecting plane, the transmission plane configured such that:
    a parallel light vertically incident on a first transmissive side of the transmission plane is transmitted thereby to reach the first reflective side of the reflecting plane, reflected thereby to reach the first reflective surface of the aspheric reflecting surface, and reflected thereby before being focused on the focal point to reach the second reflective surface of the aspheric reflecting surface to be reflected thereby to reach the second reflective side of the reflecting plane, and to be reflected thereby to reach a second transmissive side of the transmission plane to be transmitted; and
    wherein the first and second transmissive sides of the transmission plane, the first and second reflective sides of the reflecting plane, and the first and second reflective surfaces of the aspheric reflecting surface are centrosymmetric,
    wherein:
    the focal point of the aspheric reflecting surface is positioned in a location where the cells settle;
    the reflecting plane and the aspheric reflecting surface are configured such that a collimated beam generated by an external light source incident on a first reflective side of the reflecting plane is reflected thereby to reach a first reflective surface of the aspheric reflecting surface, and is reflected thereby before being focused on the focal point to reach a second reflective surface of the aspheric reflecting surface to be reflected thereby to reach a second reflective side of the reflecting plane to emerge after being reflected thereby; and
    the first and second reflective sides of the reflecting plane and the first and second reflective surfaces of the aspheric reflecting surface are centrosymmetric.

2. The sheath flow device of claim 1, wherein the aspheric reflecting surface is a rotating parabolic surface.

3. The sheath flow device of claim 1, wherein an angle between the first transmissive side and the first reflective side is 45 degrees, and wherein an angle between the second transmissive side and the second reflective side is 45 degrees.

4. The sheath flow device of claim 1, wherein the reflecting plane is a total reflecting plane.

5. The sheath flow device of claim 1, wherein the aspheric reflecting surface is coated with an optical reflective film.

6. The sheath flow device of claim 1, wherein the transmission plane, the reflecting plane, the aspheric reflecting surface, and the conduit are made of a same optical material.

7. The sheath flow device of claim 1, wherein the transmission plane is coated with an anti-reflection film.

8. The sheath flow device of claim 1, wherein the reflecting plane, the aspheric reflecting surface, and the conduit are an integrally formed structure.

9. The sheath flow device of claim 1, wherein the reflecting plane, the aspheric reflecting surface, the transmission plane, and the conduit are an integrally formed structure.

10. A hematology analyzer, comprising:
   a light source;
   an emitting optical system;
   a receiving optical system;
   a detector; and
   a sheath flow device comprising:
      a reflecting plane;
      an aspheric reflecting surface comprising a focal point;
      a conduit comprising a central hollow and configured to allow passage of blood cells disposed in the central hollow,
   wherein:
      the focal point of the aspheric reflecting surface is positioned in a location where the blood cells settle;
      the reflecting plane and the aspheric reflecting surface are configured such that a collimated beam generated by an external light source incident on a first reflective side of the reflecting plane is reflected thereby to reach a first reflective surface of the aspheric reflecting surface, and is reflected thereby before being focused on the focal point to reach a second reflective surface of the aspheric reflecting surface to be reflected thereby to reach a second reflective side of the reflecting plane to emerge after being reflected thereby; and
      the first and second reflective sides of the reflecting plane and the first and second reflective surfaces of the aspheric reflecting surface are centrosymmetric; and
      a transmission plane adjoining the reflecting plane, the transmission plane configured such that:
         a parallel light vertically incident on a first transmissive side of the transmission plane is transmitted thereby to reach the first reflective side of the reflecting plane, reflected thereby to reach the first reflective surface of the aspheric reflecting surface, and reflected thereby before being focused on the focal point to reach the second reflective surface of the aspheric reflecting surface to be reflected thereby to reach the second reflective side of the reflecting plane, and to be reflected thereby to reach a second transmissive side of the transmission plane to be transmitted; and
      wherein the first and second transmissive sides of the transmission plane, the first and second reflective sides of the reflecting plane, and the first and second reflective surfaces of the aspheric reflecting surface are centrosymmetric,
   wherein a parallel light generated by the light source is collimated by the emitting optical system before entering the sheath flow device to be focused on a position where blood cells are located therein; and
   wherein a light transmitted or scattered by the blood cells is received by the receiving optical system and output to the detector, which carries out blood analysis based on the transmitted or scattered light.

11. The hematology analyzer of claim 10, wherein the light source comprises a laser, a halogen lamp or a light-emitting diode.

12. The hematology analyzer of claim 10, wherein the emitting optical system comprises a single collimating lens.

13. The hematology analyzer of claim 10, wherein the receiving optical system comprises a single collimating lens.

* * * * *